United States Patent [19]

Chabardes

[11] Patent Number: 5,426,247
[45] Date of Patent: Jun. 20, 1995

[54] PROCESS FOR THE PREPARATION OF VITAMIN A AND INTERMEDIATE COMPOUNDS WHICH ARE USEFUL FOR THIS PROCESS

[75] Inventor: Pierre Chabardes, Saint Foy Les Lyon, France

[73] Assignee: Rhone-Poulenc Nutrition Animale, Antony, France

[21] Appl. No.: 161,509

[22] Filed: Dec. 6, 1993

[30] Foreign Application Priority Data

Dec. 17, 1992 [FR] France ................. 92 14697

[51] Int. Cl.$^6$ ............................. C07C 35/18
[52] U.S. Cl. ................... 568/824; 568/590; 568/822; 568/823
[58] Field of Search ............ 568/822, 590, 594, 824, 568/823

[56] References Cited

U.S. PATENT DOCUMENTS 4,634,778  1/1987  Mignani et al. ............ 549/80

FOREIGN PATENT DOCUMENTS

0145544A2  6/1985  European Pat. Off. .
0187259A2  7/1986  European Pat. Off. .

*Primary Examiner*—Werren B. Lone
*Attorney, Agent, or Firm*—Finnegan, Henderson, Farabow, Garrett & Dunner

[57] ABSTRACT

A process for the preparation of vitamin A which preferably comprises bringing cyclogeranyl sulphone into contact with a $C_{10}$ aldehyde acetal, halogenating the derivative obtained and then removing the halogen group and the sulphone, removing the acetal group and isomerizing the retinal obtained to the desired configuration. Also disclosed are compounds useful as intermediates in the synthesis of vitamin A and processes for preparation of these intermediate compounds.

13 Claims, No Drawings

PROCESS FOR THE PREPARATION OF VITAMIN A AND INTERMEDIATE COMPOUNDS WHICH ARE USEFUL FOR THIS PROCESS

The present invention relates to a new process for the preparation of vitamin A. As is well-understood by one skilled in the art, a reference to Vitamin A includes reference to both retinal, referred to by some as Vitamin A aldehyde, and retinol, the active compound of Vitamin A. Retinol, as is well-known by those skilled in the art, can easily be produced from retinal. The present invention also relates to new intermediates used for this synthesis.

It is known, according to the publication which appeared in the Journal of the American Chemical Society, 106, 3670 (1984), hereinafter referred to as JACS 106, to prepare vitamin A by condensation of cyclogeranyl sulphone with the methyl ester of 7-formyl-3-methyl-2,6-octadienoic acid according to the following reaction scheme:

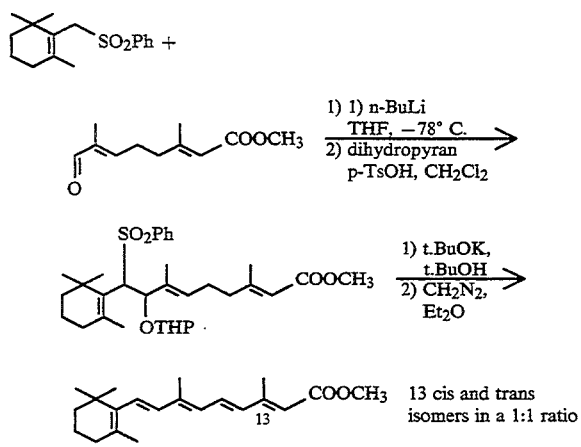

According to this publication, JACS 106, it was only possible to obtain the methyl ester of retinoic acid in a cis/trans isomer ratio, on the 13 bond, of 1/1.

In order to overcome this disadvantage, the author of this publication, JACS 106, carried out the same condensation from the corresponding $C_{10}$ alcohol in place of the methyl ester of the unsaturated $C_{10}$ acid or from the acetate of the same alcohol, using an aliphatic or aromatic hydrocarbon solvent as condensation medium.

This new process is described in particular by Otera et al. in the Journal of Organic Chemistry, 1986, 51, page 3834, hereinafter referred to as JOC 51.

The yield of vitamin A acetates obtained by this process described in JOC 51 was stated to have reached approximately 60% but required an intermediate isolation at each step, which is expensive in an industrial process. It is also necessary, in this process, to start from the $C_{10}$ intermediate in which the bonds in positions 2 and 6 are entirely trans because there is no isomerization step in this process.

It is, moreover, specified in the text of Patent EP 187,259, on page 19, which corresponds to JOC 51, that the stereochemistry of vitamin A depends on the stereochemistry of the starting compound, that is to say, the $C_{10}$ alcohol aldehyde is represented by the following formula:

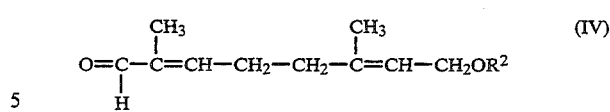

wherein $R^2$ is a lower alkanoyl group.

It is specified in Patent EP 187,259 that if the stereochemistry of the compound of formula (IV) is restricted to compounds having only 2- and 6-all-trans bonds, the stereochemistry of the vitamin A obtained will then be restricted to an all-trans stereochemistry.

The process for the preparation of vitamin A according to Patent EP 187,259 and publication JOC 51 is thus restricted, as to the unsaturated $C_{10}$ starting material, to the use of geranyl acetate, which is an expensive starting material because it is often accompanied by its 2-cis isomer which is neryl acetate. It is always difficult to obtain stereochemical (cis or trans) trisubstituted double bonds.

SUMMARY OF THE INVENTION

The process of the present invention comprises condensing cyclogeranyl sulphone with a $C_{10}$ acetal aldehyde of the following formula (I):

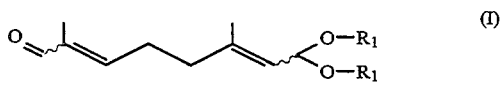

in which each $R_1$ independently represents an alkyl group preferably containing 1 to 6 carbon atoms or together both $R_1$ groups form an alkylene group preferably containing 2 to 6 carbon atoms.

The preferred compounds of formula (I) are represented by a mixture of the following four isomers:
(2E,6E)-2,6-dimethyl-octadiene-1,8-dial 8-acetal,
(2Z,6E)-2,6-dimethyl-octadiene-1,8-dial 8-acetal,
(2E,6Z)-2,6-dimethyl-octadiene-1,8-dial 8-acetal, and
(2Z,6Z)-2,6-dimethyl-octadiene-1,8-dial 8-acetal.

The compounds of formula (1) are new compounds. These compounds of formula (I) are easily obtained by oxidizing a haloacetal, preferably a chloroacetal of the following formula (II) by means of an N-oxide of a tertiary amine according to the following scheme:

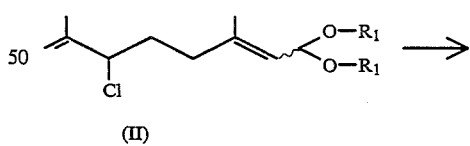

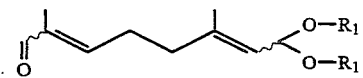

in which each $R_1$ independently represents an alkyl group containing 1 to 6 carbon atoms or together both $R_1$ groups form an alkylene group containing 2 to 6 carbon atoms.

It is preferable to use, as an oxidizing agent, the N-oxide of 4-methylmorpholine or the N-oxide of trimethylamine.

The compounds of formula (II) are obtained from citral by successive acetalizing and halogenating or successive halogenating and acetalizing reactions.

Thus, according to a first process for the preparation of a compound of formula (II), citral, shown in the following reaction scheme, is contacted with a halogenating agent such as sodium hypochlorite or gaseous chlorine in a buffered medium according to the following reaction scheme:

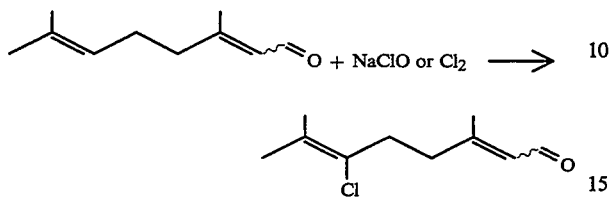

A mixture of the isomers of 3-chloro-2,6-dimethyl-1,6-octadien-8-al is obtained.

The halocitral, such as chlorocitral, is then acetalated. This acetalization is carried out in particular using a glycol, 1,3-propanediol or 1,4-butanediol in the presence of an ammonium salt such as, for example, pyridinium para-toluenesulphonate and of a trialkyl orthoformate such as trimethyl orthoformate. This method is described by Hegde et al. in Tetrahedron Letters 21, 441, (1980).

A second process for the preparation of a compound of formula (II) comprises first carrying out the acetalizing of citral and then the halogenating of the acetal obtained under the same conditions as in the first process.

A process for the preparation of vitamin A comprises:
in a first step, condensing β-cyclogeranyl sulphone with a compound of formula (I) according to the following scheme:

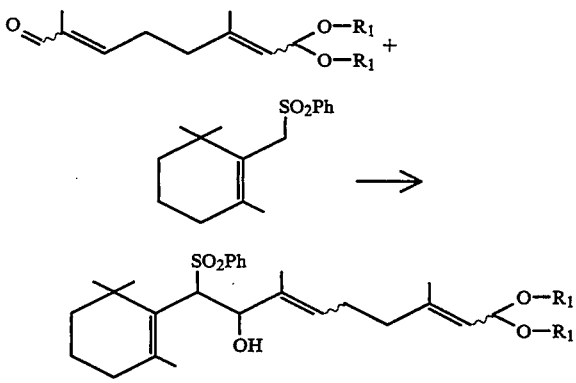

in a second step, halogenating the compound obtained in step (1) according to the following scheme:

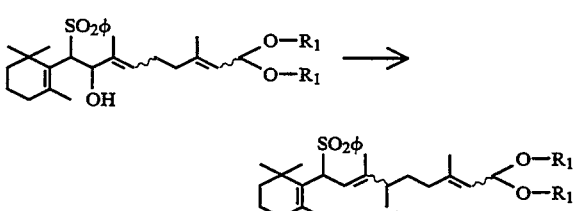

in a third step, removing both the halogen and the sulphone according to the following scheme:

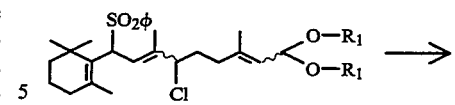

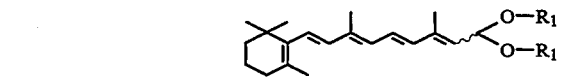

in a fourth step, removing the acetal group by hydrolyzing the acetal to form a retinal according to the following scheme:

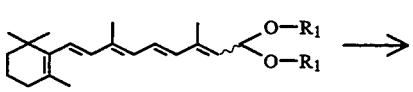

in a fifth step, isomerizing the retinal obtained in step 4 to the desired configuration.

The first step is preferably carried out in the presence of a base capable of generating a carbanion (carbonate ion) on the cyclogeranyl sulphone. Preferred bases include organolithium compounds, such as butyllithium, or organomagnesium compounds, such as methylmagnesium chloride, methylmagnesium bromide or ethylmagnesium and propylmagnesium halides. Other preferred bases include alkali metal hydrides, alkali metal amides or alkali metal alkoxides (sodium methoxide and sodium ethoxide).

The solvent of the first step is preferably a hydrocarbon solvent selected from alkanes, ethers, aromatic solvents and chlorinated solvents.

The second step is preferably carried out in the presence of thionyl chloride or phosphorous trichloride in an organic solvent in the presence of a tertiary amine.

The third step is preferably carried out in the presence of an alkali metal alkoxide in a nonpolar aprotic solvent such as a hydrocarbon, for example, toluene, cyclohexane or hexane.

Steps 1 to 3 can be carried out without being concerned with the distribution of the isomers on the vitamin A chain.

Step 4 comprises removing the acetal group so as to release the retinal. This step can be carried out in the presence of a weak acid in the quaternary ammonium form such as, for example, pyridinium p-toluenesulphonate, and of water.

The retinal obtained can be a mixture of cis and trans isomers around the 13 double bond.

The retinal can be isomerized to all-trans retinal using a complex with dihydroxybenzene and at least one of iodine or an iodine derivative, as described, for example, in U.S. Pat. No. 2,683,746, U.S. Pat. No. 2,693,747 or French Patent No. 1,291,622, the disclosures of which are expressly incorporated by reference herein.

It is preferable to carry out the isomerization in the presence of hydroquinone and iodine or hydriodic acid.

By the process of the present invention, it is possible in the same reactor, from the $C_{10}$ aldehyde acetal of formula (I), to obtain a mixture of 13 cis/13 trans isomers of retinal without isolating any intermediate,

5 which is a tremendous advantage from an industrial viewpoint.

DESCRIPTIONS OF PREFERRED EMBODIMENTS

The present invention will be described more completely with the aid of the following examples which should not be regarded as limiting the invention.

EXAMPLE 1

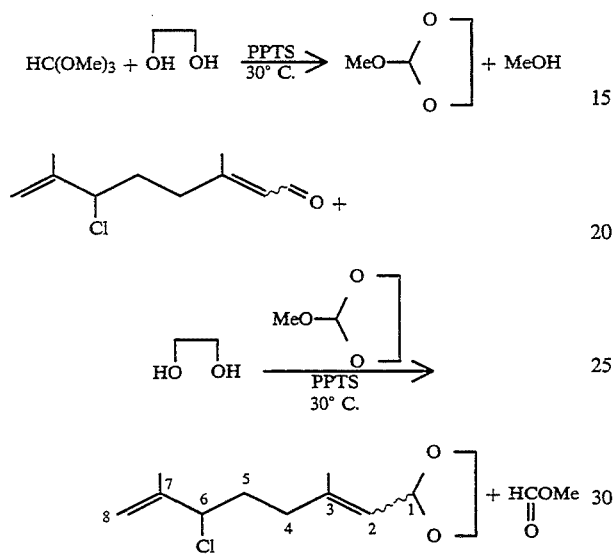

The following were charged to a 25 ml round-bottomed flask equipped with a stirrer, a distillation extension and a 5 ml receiver:
 0.067 g of 98% pyridinium 15 toluenesulphonate
 0.698 g of 97% trimethyl orthoformate
 4 ml of ethylene glycol.

Stirring began and the apparatus was placed under vacuum (approximately 100 mbar) and the mixture was heated at 30° C. for 1 hour 30 minutes. 1.02 g of 95% chlorocitral was then run in dropwise using a syringe which was then rinsed with 0.5 ml of ethylene glycol. The mixture was stirred for 3 hours at 30° C. and then cooled before it was extracted with pentane. The organic phase was washed several times with a saturated sodium bicarbonate solution (ph=8–9) and then with a saturated sodium chloride solution (ph=6–7). The organic phase was dried over magnesium sulphate and concentrated. The residual bright yellow liquid was purified by preparative chromatography (phase: Florisil VD 0.075–0.150 mm, eluant: pentane 100 ml–9/1 pentane/ether 200 ml–8/2 pentane/ether 100 ml). There was obtained 0.507 g of a colorless liquid identified by NMR as being the expected structure (2 isomers): Yield: 40%.

| NMR: 360 MHz $^1$H NMR (CDCl$_3$-Ref. HMDS) | | |
|---|---|---|
| δ (ppm) | H⁻ | Attribution |
| 1.7 to 2.3 | 10 H⁻ | 2H$_4$—2H$_5$—6H (methyl) |
| 3.86 | 4 H | Glycolic acetal |
| 3.98 | | |
| 4.33 | 1 H | H$_6$ (cis + trans) |
| 4.88 | | trans |
| 4.99 | 2 H | H$_8$ |
| 4.88 | | cis |
| 5.01 | | |
| 5.25 | 1 H | H$_2$ trans |

| NMR: 360 MHz $^1$H NMR (CDCl$_3$-Ref. HMDS) | | |
|---|---|---|
| δ (ppm) | H⁻ | Attribution |
| 5.28 | | cis |
| 5.44 | 1 H | H$_1$ cis |
| 5.47 | | trans |

EXAMPLE 2

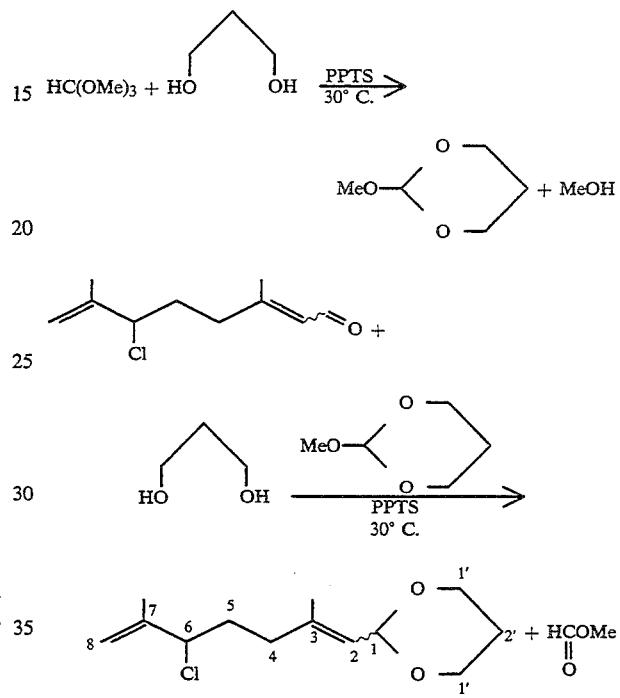

The following were charged to a 250 ml four-necked flask equipped with a stirrer, a thermometer, 25 ml dropper funnel, an extended distillation head, a reflux condenser and a 100 ml receiver:
 0.758 g of 98% pyridinium p-toluenesulphonate
 55 ml of 1,3-propanediol
 9 ml of 97% trimethyl orthoformate The mixture was stirred and the apparatus was put under vacuum (approximately 100 mbar) and the mixture was heated at 30° C. for 1 hour 30 minutes.

The vacuum was shut off and an argon circulation was set up. 10.964 g of 95% chlorocitral diluted in 7 ml of anhydrous THF was slowly added (10 min duration). The dropping funnel was rinsed with 3 ml of THF and the mixture was allowed to stir at 30° C. for 2 hours 30 minutes. The mixture was cooled to 20° C., extracted with a 1/10 ether/pentane mixture and washed successively with a saturated sodium bicarbonate solution and a saturated sodium chloride solution. The organic phase was dried over magnesium sulphate and concentrated. The yellow liquid obtained was passed through a preparative column (phase: Florisil Φ0.075–0.150 mm, eluant: pentane-1/1 pentane/ether gradient).

There was obtained 10.99 g of chloroacetal identified by NMR. Yield: 80% (trans: 67%—cis: 33% isomers).

| NMR: 360 MHz $^1$H NMR (CDCl$_3$-Ref. HMDS) | | |
|---|---|---|
| δ (ppm) | H | Attribution |
| 1.2 to 2.2 | 12 H | 2H$_2$,—2H$_5$—2H$_4$—6H (methyl) |

-continued

| NMR: 360 MHz $^1$H NMR (CDCl$_3$-Ref. HMDS) | | |
|---|---|---|
| δ (ppm) | H | Attribution |
| 3.77 | 2 H | 2H$_1$, axial |
| 4.06 | 2 H | 2H$_1$, equatorial |
| 4.28 | 1 H | 1H$_6$ (cis + trans) |
| 4.82 |  | trans |
| 4.94 | 2 H | H$_8$ |
| 4.84 |  | cis |
| 4.97 |  |  |
| 5.12 | 1 H | H$_1$ cis |
| 5.13 |  | trans |
| 5.22 | 1 H | H$_2$ trans |
| 5.26 |  | cis |

EXAMPLE 3

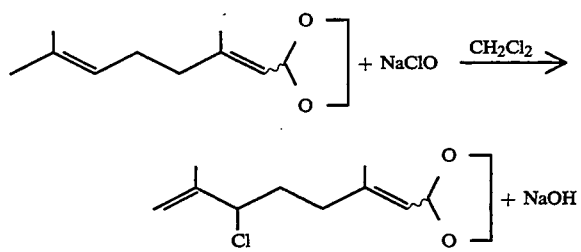

The following were charged to a 500 ml three-necked flask equipped with a stirrer, a thermometer, a pH-meter probe and a dropping funnel:

12.84 g of citral glycol acetal
160 ml of dichloromethane.

The mixture was cooled in an ice bath. 89 ml of bleach (at 0.94 mol.l$^{-1}$) was slowly added. The pH was maintained between 7 and 8 by addition of solid carbon dioxide and the temperature remained between 0° and 10° C. The mixture was allowed to stir for 3 hours at this temperature. 150 ml of water was then added and the mixture was extracted several times with dichloromethane. The organic phase was then washed successively with a 10% sodium sulphite solution and a saturated sodium bicarbonate solution.

After drying over MgSO$_4$ and concentration, there was obtained 14.73 g of a pale-yellow liquid analyzed by GPC. The chloroacetal yield was approximately 80% (calculated from the GPC surface area ratios). The NMR was identical to that of Example 1.

EXAMPLE 4

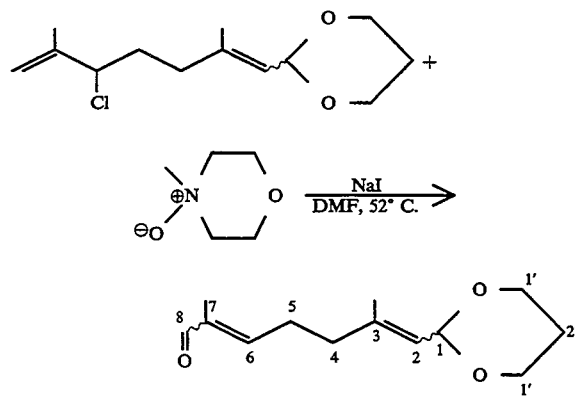

The following were charged to a 250 ml four-necked flask equipped with a stirrer and a thermometer and purged with argon:

6.021 g of 90% chloroacetal
40 ml of anhydrous DMF
4.042 g of sodium iodide
7.51 g of anhydrous 97% 4-methylmorpholine N-oxide.

The mixture was stirred for 5 hours at 52° C. The round-bottomed flask was immersed in an ice bath and then ether and a saturated sodium bicarbonate solution were added.

Extraction was carried out with ether and the extract was washed several times with a sodium bicarbonate solution and then a saturated sodium chloride solution.

The organic phase was dried over magnesium sulphate and concentrated. The residual orange liquid was chromatographed on a column (phase: Florisil Φ0.075–0.150 mm, eluant: 10/1 pentane/ether-ether gradient).

There was obtained 3.149 g of a pale yellow liquid identified by NMR as being the expected aldehyde acetal (mixture of 4 isomers). Yield: 56%.

| NMR: 360 MHz $^1$H NMR (CDCl$_3$-Ref. HMDS) | | |
|---|---|---|
| δ (ppm) | H | Attribution |
| 1.29 | 1 H | H$_2$, equatorial |
| 1.7 to 2.8 | 11 H | H$_2$, axial-2H$_5$—2H$_4$—6H (methyl) |
| 3.77 | 2 H | H$_1$, axial |
| 4.07 | 2 H | H$_1$, equatorial |
| 5.25 | 1 H | H$_2$ |
| 5.29 |  |  |
| 6.42 | 1 H | H$_6$ |
| 6.47 |  |  |

| δ H$_8$ | δ H$_1$ | Isomer |
|---|---|---|
| 10.08 | 5.13 | 2E, 6Z |
| 10.05 | 5.07 | 2Z, 6Z |
| 9.34 | 5.08 | 2Z, 6E |
| 9.32 | 5.14 | 2E, 6E |

EXAMPLE 5

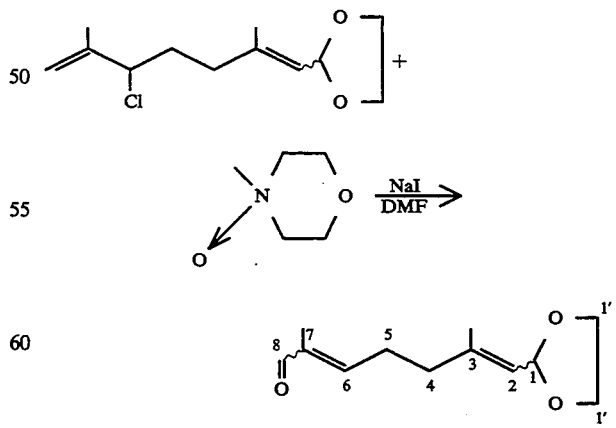

By carrying out the reaction in a way analogous to that of Example 4, there was obtained a mixture of the four isomers of the C$_{10}$ aldehyde acetal characterized by NMR analysis.

| NMR: 360 MHz ¹H NMR (solvent CDCl₃-Ref. HMDS) | | |
|---|---|---|
| δ (ppm) | H⁻ | Attribution |
| 1.6 to 2.6 | 10 H⁻ | 2H₄—2H₅—6H (methyl) |
| 3.8 to 4.1 | 4 H | 2 × 2 |
| 5.28 | | |
| 5.32 | 1 H | 1H₂ (cis and trans) |
| approximately 5.4 to 5.5 1 H | 1 H₁ | 1H₁ (cis and trans) |
| 9.38 | | |
| 9.39 | | H₈ trans (cis-trans acetal isomers) |
| 9.45 | 1 H | |
| 9.46 | | H₈ cis (cis-trans acetal isomers) |

EXAMPLE 6

STEP 1 : OXIDATION

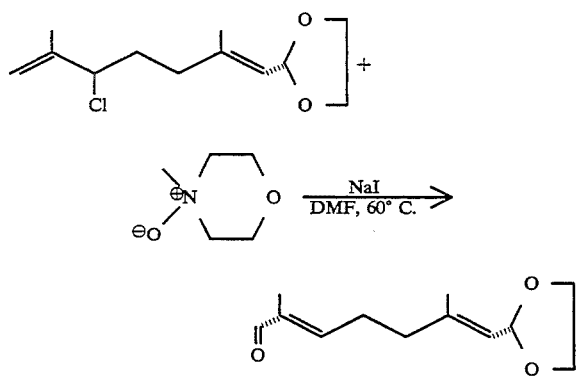

STEP 2 : ANIONIZATION

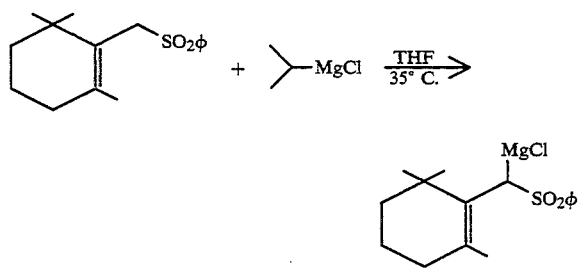

STEP 3 : CONDENSATION

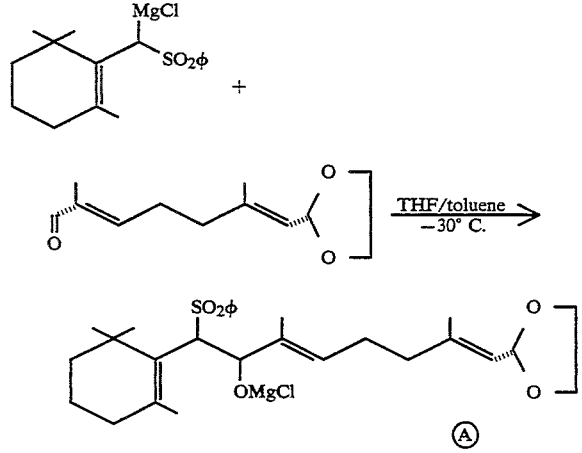

STEP 4 : CHLORINATION

 + SOCl₂ $\xrightarrow[\text{THF/toluene}]{\text{pyridine}}$

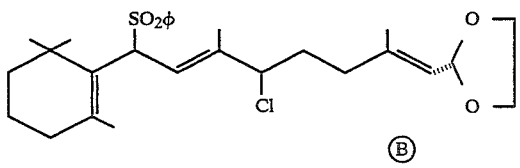

STEP 5 : DOUBLE REMOVAL

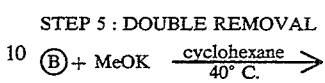 + MeOK $\xrightarrow[\text{40° C.}]{\text{cyclohexane}}$

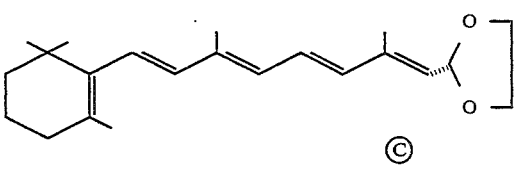

STEP 6 : DEACETALIZATION

ⓒ + PPTS $\xrightarrow[\text{40° C.}]{\text{THF/H}_2\text{O}}$

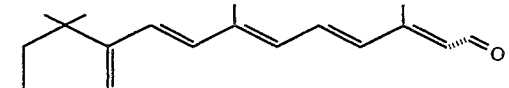

13 cis/13 trans retinal

STEP 1

The following were charged to a 25 ml two-necked flask equipped with a thermometer and a stirrer and purged with argon:

0.779 g of anhydrous 97% 4-methylmorpholine N-oxide
0.450 g of sodium iodide
0.585 g of glycol chloroacetal
5.5 ml of anhydrous DMF.

The mixture was heated at 60° C. for 4 hours 30 minutes and was then cooled in an ice bath, extracted with ether and washed successively with saturated sodium bicarbonate and sodium chloride (ph=7) solutions.

4 ml of toluene were added to the organic phase and the ether was evaporated.

STEP 2

The following were charged to a 50 ml two-necked flask equipped with a stirrer, a thermometer and a 10 ml dropping funnel and purged with argon:

0.825 g of 95% cyclogeranyl phenyl sulphone
7 ml of anhydrous THF
1.35 ml of a 2M solution of isopropylmagnesium chloride in THF.

The mixture was stirred for 3 hours 30 minutes at 35° C.

STEP 3

The three-necked flask of Step 2 was immersed in a bath at −30°/−35° C. The solution of the aldehyde glycol acetal in toluene (cf. Step 1) was charged into the dropping funnel. This aldehyde was run in over 7 min and the dropping funnel was rinsed with 1.5 ml of toluene. The mixture was stirred for 1 hour 45 minutes at −30° C.

STEP 4

0.540 ml of anhydrous pyridine was added and then 0.250 ml of thionyl chloride was run in. The mixture was allowed to react at −30° C. for 45 minutes and then for 45 minutes at 0° C.

20 ml of ice-cold water were poured into the reaction mixture. Extraction was carried out with toluene and the extract was washed with a saturated sodium bicarbonate solution (pH 8/9) and then a sodium chloride solution (pH 6/7).

The organic phase was dried over MgSO$_4$.

After the evaporation of the toluene, there was obtained 1.534 g of a cloudy orange liquid purified by chromatography (phase: Florisil Φ0.075–0.150 mm, eluant: 20/80% AcOEt/pentane). There was obtained 0,597 g of a mixture of chlorinated sulphones C$_{20}$ acetals and aldehydes. Yield of the order of 45 to 50%.

STEP 5

The following were charged to a 25 ml round-bottomed flask equipped with a stirrer and purged with argon:
- 0.560 g of the mixture obtained in Stage 4.
- 15 ml of cyclohexane
- 0.838 g of 95% potassium methoxide.

The mixture was stirred for 3 hours at 40° C. and then hydrolyzed with a saturated ammonium chloride solution at 25° C. Extraction was carried out with isopropyl ether. Washing was carried out with a saturated sodium chloride solution (pH at 6–7).

After drying over MgSO$_4$ and removal of the solvent, there was obtained 0.362 g of a bright red oil.

NMR quantitative determination with an internal standard (p-dimethoxybenzene) gave the following distribution:
- acetal of 13 cis+13 trans retinal: 34% (by mass)
- 13 cis+13 trans retinal: 10%

Yield: 21% (calculated based on the C$_{10}$ chloroacetal).

STEP 6

The following were charged to a 50 ml round-bottomed flask equipped with a stirrer:
- 0.289 g of the crude product resulting from step 5
- 5 ml of THF
- 0.9 ml of water
- 0.012 g of pyridinium p-toluenesulphonate.

The mixture was stirred for 1 hour 30 minutes at room temperature while excluded from the light. After being extracted with ether, washed with saturated NaHCO$_3$ and NaCl solutions, dried over MgSO$_4$ and the evaporation of the solvent, there was obtained 0,266 g of a red oil which was purified by chromatography (phase: silica, eluant: 10/1 pentane/ether). There was obtained 0.100 g of retinal (78% all-trans isomer, 22% 13 cis isomer). Yield: 18% (calculated based on the C$_{10}$ chloroacetal).

EXAMPLE 7

Steps 2 to 6 were linked together, without isolating any intermediate.

STEPS 2 to 4

The following were charged to a 50 ml three-necked flask equipped with a 10 ml dropping funnel and a stirrer and purged with argon:
- 0.81 g of 95% cyclogeranyl phenyl sulphone
- 7 ml of anhydrous THF
- 1.4 ml of a 2M solution of isopropylmagnesium chloride in THF.

The mixture was stirred for 1 hour 10 minutes at 35° C. It was cooled to −30° C. and 0.627 g of 95% aldehyde acetal obtained according to Step 1 of Example 6, as a solution in 6 ml of anhydrous toluene, was charged into the dropping funnel.

This solution was introduced into the reaction mixture over 10 minutes. The mixture was allowed to stir for 2 hours at −30° C. and then 0.560 ml of pyridine was added (in a single step). 0.260 ml of thionyl chloride was then charged dropwise. The mixture was allowed to react for 1 hour at −30° C. and 1 hour at 0°/5° C. The reaction mass was subjected to extractions with toluene and the extracts were washed with saturated sodium bicarbonate and sodium chloride solutions.

The organic phase was concentrated. There was obtained an orange oil which was placed in a 10 ml round-bottomed flask with 40 ml of cyclohexane.

STEP 5

The round-bottomed flask was purged with argon, 1.964 g of potassium methoxide was charged and the mixture stirred at 40° C. for 3 hours.

The reaction mass was extracted with isopropyl ether and washed successively with ammonium chloride and sodium chloride solutions.

The organic phase was concentrated in a 50 ml round-bottomed flask.

STEP 6

The following were added to the above round-bottomed flask:
- 15 ml of THF
- 2 ml of water
- 40 mg of pyridinium p-toluenesulphonate.

The mixture was allowed to stir for 1 hour 30 minutes at room temperature. It was extracted with ether. The ether extracts were washed several times with saturated sodium bicarbonate and sodium chloride (ph=6–7) solutions.

The organic phase was dried over magnesium sulphate and concentrated. There was obtained 1.054 g of an orange-yellow oil which was purified on a silica column (phase: amicon silica Φ0.020–0.045 mm, eluant: 1/7 ether/pentane).

The recovered product contained 0.394 g of retinal, i.e. a yield (with respect to the aldehyde acetal) of 52% with the distribution:

| | |
|---|---|
| -all-trans | 46% |
| -13 cis | 49% |
| -other | <5% |

The 2,3 double bond of the starting C$_{10}$ acetal was:

| | |
|---|---|
| -trans | 48% |
| -cis | 52%. |

STEP 7

The preceding mixture of isomers was taken up and dissolved in 2 ml of ethyl ether. 100 mg of hydroquinone was added. After agitation 0.1 ml of hydriodic acid was added. The mixture was allowed to stand overnight and filtered and 0.33 g of complex was obtained.

The complex obtained was introduced into 2 ml of methanol-water solution (90–10) into which 10 mg of sodium borohydride was added. The retinol obtained (340 mg) was analyzed by liquid chromatography. It showed the following distribution:

| -all-trans | 95.5% |
|---|---|
| -13 cis | 4% |
| -9 cis | 0.5% |

What is claimed is:

1. A process for the preparation of vitamin A, which comprises:

in a first step, condensing cyclogeranyl sulphone with a compound of formula (I) according to the following scheme:

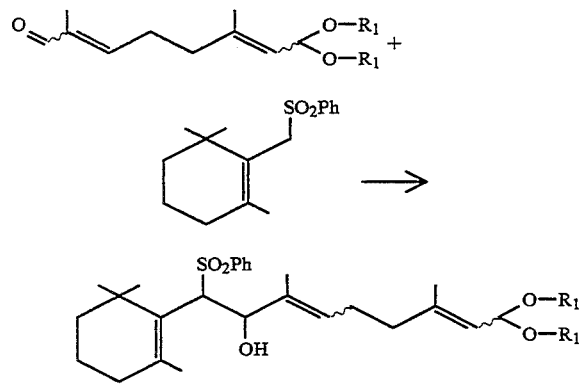

in which Ph is phenyl and each $R_1$ independently represents an alkyl group containing 1 to 6 carbon atoms or together both $R_1$ groups form an alkylene group containing 2 to 6 carbon atoms, in a second step, halogenating the compound obtained in step 1 according to the following scheme:

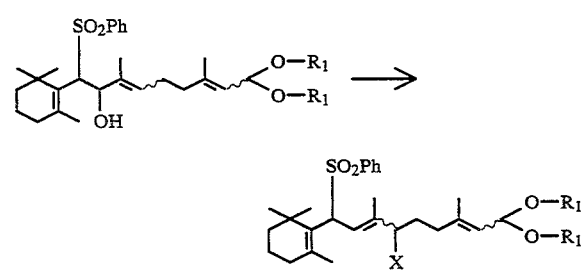

in which X is halogen, in a third step, removing both the sulphone group and the halogen according to the following scheme:

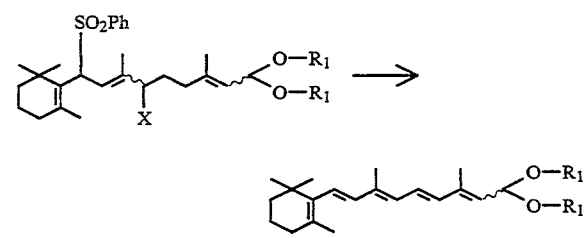

in a fourth step, removing the acetal group to form a retinal according to the following scheme:

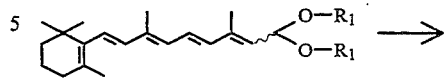

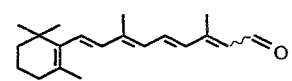

in a fifth step, isomerizing the retinal obtained in step 4 to the desired configuration of vitamin A.

2. A process according to claim 1, wherein the first step is carried out in a hydrocarbon solvent in the presence of a base.

3. A process according to claim 2, wherein the hydrocarbon solvent is selected from alkanes, ethers, aromatic solvents and chlorinated solvents.

4. A process according to claim 2, wherein the base is capable of generating a carbonate ion on the cyclogeranyl sulphone and is selected from an organolithium compound, an organomagnesium compound, an alkali metal hydride, an alkali metal amide and an alkali metal alkoxide.

5. A process according to claim 1, wherein the second step is carried out in the presence of thionyl chloride or phosphorus trichloride and in the presence of a tertiary amine.

6. A process according to claim 1, wherein the third step is carried out in the presence of an alkali metal alkoxide in a nonpolar aprotic solvent.

7. A process according to claim 1, wherein the fourth step is carried out in the presence of a quaternary ammonium compound.

8. A process according to claim 1, wherein the fifth step is carried out in the presence of a dihydroxybenzene and at least one of iodine or an iodine derivative.

9. A process according to claim 1, wherein the fifth step is carried out in the presence of hydroquinone and iodine or hydriodic acid.

10. A process for the preparation of vitamin A, which comprises:

in a first step, condensing cyclogeranyl sulphone with a compound of formula (I), according to the following scheme:

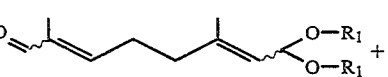

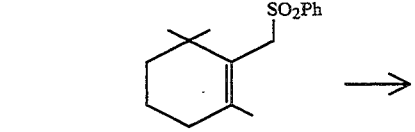

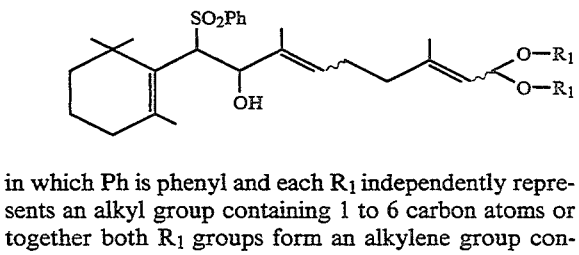

in which Ph is phenyl and each $R_1$ independently represents an alkyl group containing 1 to 6 carbon atoms or together both $R_1$ groups form an alkylene group containing 2 to 6 carbon atoms, in a hydrocarbon solvent in the presence of a base, in a second step, chlorinating the compound obtained in step 1, utilizing thionyl chloride or phosphorous trichloride in the presence of a tertiary amine, according to the following scheme:

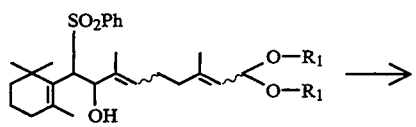

→

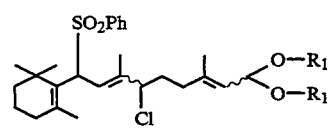

in a third step, removing both the sulphone group and the chlorine, in the presence of an alkali metal alkoxide in a hydrocarbon, according to the following scheme:

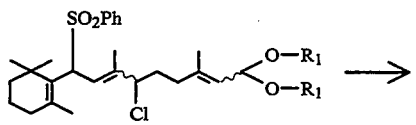

→

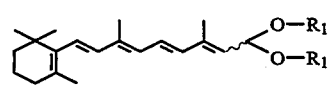

in a fourth step, removing the acetal group to form a retinal, in the presence of a quaternary ammonium compound, according to the following scheme:

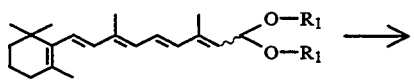

→

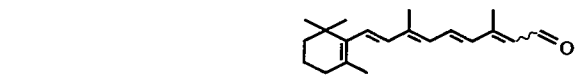

and in a fifth step, isomerizing the retinal obtained in step 4, in the presence of a dihydroxybenzene and at least one of iodine or an iodine derivative to obtain vitamin A.

11. A process according to claim 10, wherein said dihydroxtbensene is hydroquinone and wherein said iodine derivative is hydriodic acid.

12. A process for the preparation of a compound of formula (I):

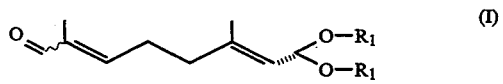 (I)

which comprises contacting the compound of formula (II):

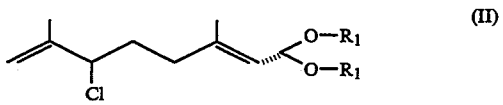 (II)

in which $R_1$ represents an alkyl group containing 1 to 6 carbon atoms or together both $R_1$ groups form an alkylene group containing 2 to 6 carbon atoms, with an N-oxide of a tertiary amine to prepare a compound of formula (I).

13. A process according to claim 12, wherein the tertiary amine is 4-methylmorpholine or trimethylamine.

* * * * *

UNITED STATES PATENT AND TRADEMARK OFFICE
CERTIFICATE OF CORRECTION

PATENT NO. : 5,426,247
DATED : June 20, 1995
INVENTOR(S) : Pierre CHABARDES

It is certified that error appears in the above-indentified patent and that said Letters Patent is hereby corrected as shown below:

Claim 11, column 16, line 16, "dihydroxtbensene" should read --dihydroxybenzene--.

Signed and Sealed this

Fourteenth Day of May, 1996

Attest:

BRUCE LEHMAN

Attesting Officer    Commissioner of Patents and Trademarks